(12) United States Patent
Hasegawa et al.

(10) Patent No.: US 12,716,886 B2
(45) Date of Patent: Aug. 25, 2026

(54) BIOLOGICAL INFORMATION MEASUREMENT DEVICE, BIOLOGICAL INFORMATION MEASUREMENT METHOD, AND COMPUTER-READABLE RECORDING MEDIUM

(71) Applicants: FURUKAWA ELECTRIC CO., LTD., Tokyo (JP); TOHOKU UNIVERSITY, Sendai (JP)

(72) Inventors: Hideaki Hasegawa, Tokyo (JP); Takayori Ito, Tokyo (JP); Hiroyuki Tamaoka, Tokyo (JP); Koji Kawajiri, Tokyo (JP); Rihito Kuroda, Miyagi (JP)

(73) Assignees: FURUKAWA ELECTRIC CO., LTD., Tokyo (JP); TOHOKU UNIVERSITY, Sendai (JP)

( * ) Notice: Subject to any disclaimer, the term of this patent is extended or adjusted under 35 U.S.C. 154(b) by 262 days.

(21) Appl. No.: 18/450,628

(22) Filed: Aug. 16, 2023

(65) Prior Publication Data

US 2023/0393117 A1 Dec. 7, 2023

Related U.S. Application Data

(63) Continuation of application No. PCT/JP2022/006499, filed on Feb. 17, 2022.

(30) Foreign Application Priority Data

Feb. 18, 2021 (JP) ................................. 2021-024344

(51) Int. Cl.
*G01N 33/49* (2006.01)
*B01L 3/00* (2006.01)
(Continued)

(52) U.S. Cl.
CPC ........ *G01N 33/49* (2013.01); *B01L 3/502715* (2013.01); *G01N 15/06* (2013.01);
(Continued)

(58) Field of Classification Search
CPC .... G01N 33/49; G01N 15/06; G01N 15/1429; G01N 15/1433; G01N 15/01;
(Continued)

(56) References Cited

U.S. PATENT DOCUMENTS 6,329,139 B1 * 12/2001 Nova ..................... B82Y 10/00 506/40
2010/0185068 A1 * 7/2010 Park .................. A61B 5/02433 600/323
(Continued)

FOREIGN PATENT DOCUMENTS

JP 2005-106592 A 4/2005
JP 2006-122579 A 5/2006
(Continued)

OTHER PUBLICATIONS

International Search Report issued May 24, 2022 in PCT/JP2022/006499 filed on Feb. 17, 2022, 4 pages.

*Primary Examiner* — Sang H Nguyen
(74) *Attorney, Agent, or Firm* — Oblon, McClelland, Maier & Neustadt, L.L.P.

(57) ABSTRACT

A biological information measurement device includes: a scattering rate calculating unit configured to calculate a scattering rate of light at an interface between a medium present in a biological object or in a specimen and a particle included in the medium based on received-light intensity of light irradiated onto the biological object or onto the specimen and received via the biological object or via the specimen; and a concentration index calculating unit configured to calculate, based on a correlation between the
(Continued)

scattering rate of the light at the interface and a concentration index corresponding to concentration of a target substance that is different from the particle included in the medium, the concentration index corresponding to the scattering rate of the light calculated by the scattering rate calculating unit.

19 Claims, 6 Drawing Sheets

(51) Int. Cl.

| | |
|---|---|
| ***G01N 15/06*** | (2024.01) |
| ***G01N 15/14*** | (2024.01) |
| ***G01N 15/1429*** | (2024.01) |
| ***G01N 15/1433*** | (2024.01) |
| *G01N 15/01* | (2024.01) |
| *G01N 15/075* | (2024.01) |

(52) U.S. Cl.
CPC ..... *G01N 15/1429* (2013.01); *G01N 15/1433* (2024.01); *B01L 2300/0654* (2013.01); *B01L 2300/168* (2013.01); *G01N 15/01* (2024.01); *G01N 15/075* (2024.01); *G01N 2015/1493* (2013.01)

(58) Field of Classification Search
CPC ......... G01N 15/075; G01N 2015/1493; G01N 2015/0687; G01N 21/4738; G01N 21/4788; G01N 2021/1765; B01L 3/502715; B01L 2300/0654; B01L 2300/168; A61B 5/14532; A61B 5/1455
See application file for complete search history.

(56) References Cited

U.S. PATENT DOCUMENTS

2014/0350365 A1 11/2014 Sato
2015/0313516 A1* 11/2015 Shimizu ............. A61B 5/14546 600/322
2016/0157733 A1* 6/2016 Gil ..................... A61B 5/14551 600/316
2017/0027526 A1* 2/2017 Maruo ............... A61B 5/14532
2017/0353672 A1 12/2017 Nakamura et al.
2020/0353150 A1* 11/2020 Barrett .................... A61M 1/36

FOREIGN PATENT DOCUMENTS

JP 2008-253455 A 10/2008
JP 2017-220926 A 12/2017
WO WO 2013/094362 A1 6/2013

* cited by examiner

START

S1: IRRADIATED LIGHT AND RECEIVE LIGHT

S2: CALCULATE RECEIVED-LIGHT INTENSITY

S3: CALCULATE SCATTERING RATE OF LIGHT

S4: CALCULATE CONCENTRATION INDEX

S5: OUTPUT RESULT

END

BIOLOGICAL INFORMATION MEASUREMENT DEVICE, BIOLOGICAL INFORMATION MEASUREMENT METHOD, AND COMPUTER-READABLE RECORDING MEDIUM

This application is a continuation of International Application No. PCT/JP2022/006499, filed on Feb. 17, 2022 which claims the benefit of priority of the prior Japanese Patent Applications No. 2021-024344, filed on Feb. 18, 2021, the entire contents of which are incorporated herein by reference.

BACKGROUND

The present disclosure relates to a biological information measurement device, a biological device measurement method, and a computer-readable recording medium.

In the related art, a method is known for noninvasive measurement of blood components using light (for example, Japanese Patent Application Laid-open No. 2005-106592). In the method disclosed in Japanese Patent Application Laid-open No. 2005-106592, the concentration of the target substance for measurement is detected according to the absorption of light by that substance.

SUMMARY

In a method that makes use of the absorption of light by the target substance, such as the method disclosed in Japanese Patent Application Laid-open No. 2005-106592; the scattering of light occurring due to the refractive index difference between the substances other than the target substance and the surrounding substances gets measured as noise, and that leads to a decline in the measurement accuracy.

There is a need for a biological information measurement device, a biological information measurement method, and a program in a new and improved form for enabling measurement with a higher degree of accuracy.

According to one aspect of the present disclosure, there is provided a biological information measurement device including: a scattering rate calculating unit configured to calculate a scattering rate of light at an interface between a medium present in a biological object or in a specimen and a particle included in the medium based on received-light intensity of light irradiated onto the biological object or onto the specimen and received via the biological object or via the specimen; and a concentration index calculating unit configured to calculate, based on a correlation between the scattering rate of the light at the interface and a concentration index corresponding to concentration of a target substance that is different from the particle included in the medium, the concentration index corresponding to the scattering rate of the light calculated by the scattering rate calculating unit.

According to another aspect of the present disclosure, there is provided a biological information measurement method executed by a computer including: calculating a scattering rate of light at an interface between a medium present in a biological object or in a specimen and a particle included in the medium based on received-light intensity of light irradiated onto the biological object or onto the specimen and received via the biological object or via the specimen; and calculating the concentration index as biological information calculating performing correction in form of subtracting the calculated scattering rate of light based on a correlation stored in a memory and established between the scattering rate of light at the interface and a concentration index corresponding to concentration of a target substance that is different from the particle included in the medium.

According to still another aspect of the present disclosure, there is provided a biological information measurement method executed by a computer including: calculating feature quantity regarding an area of interface or a boundary length of interface in a particle image of a particle by performing image processing of a two-dimensional image of a medium of a biological object or a specimen including the particle and a target substance; and calculating a concentration index corresponding to the calculated feature quantity of the particle image based on a correlation established between the feature quantity of the particle image and concentration index corresponding to concentration of the target substance included in the medium, the correlation corresponding to a fact that density of the particle in the medium decreases in inverse proportion to an increase in concentration of the target substance.

According to yet another aspect of the present disclosure, there is provided a biological information measurement method executed by a computer including: calculating feature quantity regarding an area of interface or a boundary length of interface of a particle by performing laser diffraction/scattering method to a medium of a biological object or a specimen including the particle and a target substance; and calculating a concentration index corresponding to the calculated feature quantity of the particle image based on a correlation established between the feature quantity and concentration index corresponding to concentration of the target substance included in the medium, the correlation corresponding to a fact that density of the particle in the medium decreases in inverse proportion to an increase in concentration of the target substance.

DETAILED DESCRIPTION

Exemplary embodiments are described below. The configurations explained in the embodiments described below as well as the actions and the results (effects) attributed to the configurations are only exemplary. Thus, the present disclosure may be implemented also using some different configuration than the configurations disclosed in the embodiments described below. Meanwhile, according to the present disclosure, it becomes possible to achieve at least one of various effects (including secondary effects) that are attributed to the configurations.

In the present written description, the scattering of light particularly implies the case in which, only at the concerned wavelength, particles do not have a peak that results in a decline in the light transmission rate; and in which the light transmission rate either goes on continuously declining or remains at a constant value more toward the side of shorter wavelengths within a range of around ±50 [nm] of the concerned wavelength. Moreover, there is also an occurrence of light loss at the interface between the particles and the substance. Academically, there have been reports that, at the interface of particle such as blood cells, local absorption also occurs besides the scattering. However, in practice, the loss of the transmitted light occurring at the interface is extremely difficult to isolate as scattering or absorption. In that regard, in the present written description, all of the loss attributed to the particle interface and having wavelength dependency is defined as the light loss.

Moreover, in the present written description, the scattering rate of light indicates the proportion of the input of the attenuated light generated due to the scattering of light with respect to the intensity of "1" of the input light, as well as indicates all physical quantities that have a correlation with that proportion. For example, the scattering rate of light may be a Reyleigh scattering coefficient or a Mie scattering coefficient.

Figure 1:
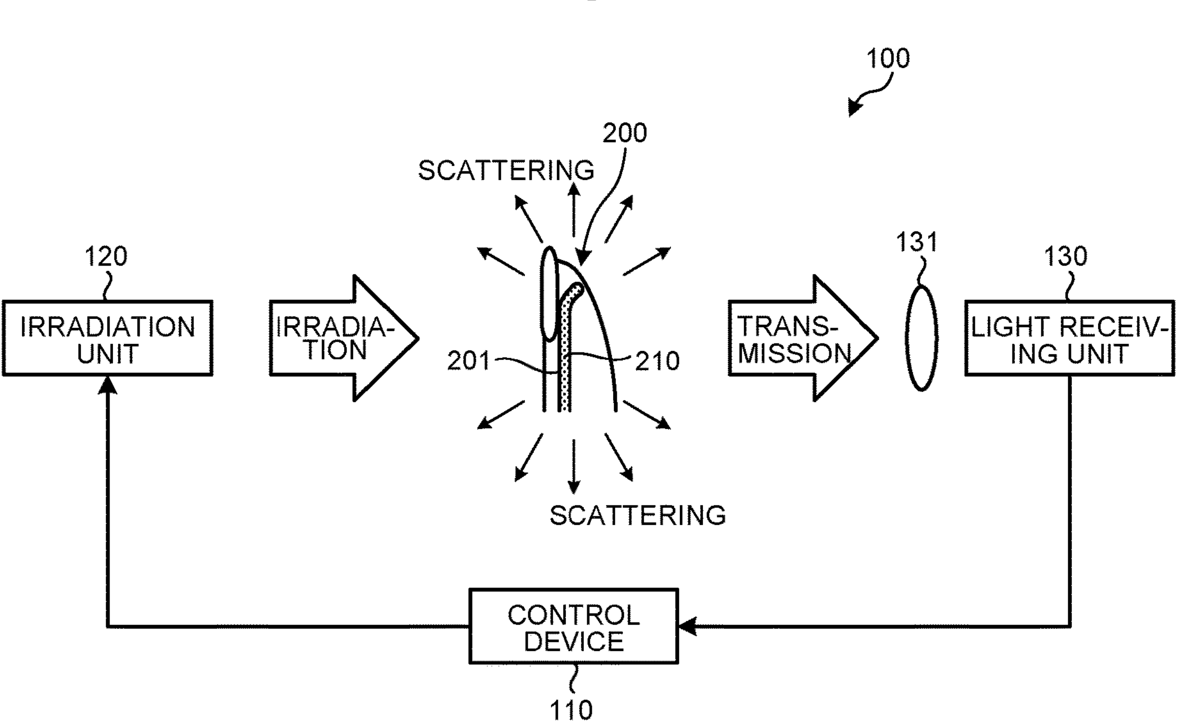
FIG. 1 is an illustrative overall configuration diagram of a biological information measurement device according to a first embodiment.

FIG. 1 is an overall configuration diagram of a biological information measurement device 100. As illustrated in FIG. 1, the biological information measurement device 100 includes a control device 110, an irradiation unit 120, a light receiving unit 130, and a field lens 131.

The control device 110 controls the constituent elements of the biological information measurement device 100 and, based on a testing light received by the light receiving unit 130, carries out testing of blood 210 included in a blood vessel 201 of a biological object 200. Herein, as an example, the glucose concentration is tested. The blood 210 may also be referred to as a test material. In the blood 210; blood plasma, blood cells, and glucose are included. The blood plasma represents an example of a medium; the blood cells represent an example of particles; and the glucose represents an example of the target substance.

The irradiation unit 120 irradiates the biological object 200 with the testing light. The irradiation unit 120 includes a light source device and an optical-system component that transmits the testing light coming from the light source device and emits it.

The light receiving unit 130 either receives the testing light that was irradiated onto the biological object 200 and that came from the biological object 200. For example, the light receiving unit 130 receives the testing light that has passed through the biological object 200, or receives the reflected light that got reflected from the biological object 200. For example, the light receiving unit 130 includes a light receiving element such as a CMOS image sensor or a CCD, and includes an optical system component that transmits the testing light to the light receiving element. Meanwhile, the measurement target onto which the testing light is irradiated is not limited to the biological object 200, and alternatively may be a specimen that includes the substances of the biological object 200.

The field lens 131 allows passage of the light that is input to the light receiving unit 130 from the blood 210. As a result of using the field lens 131, it becomes possible to enhance the resolution.

Figure 2:
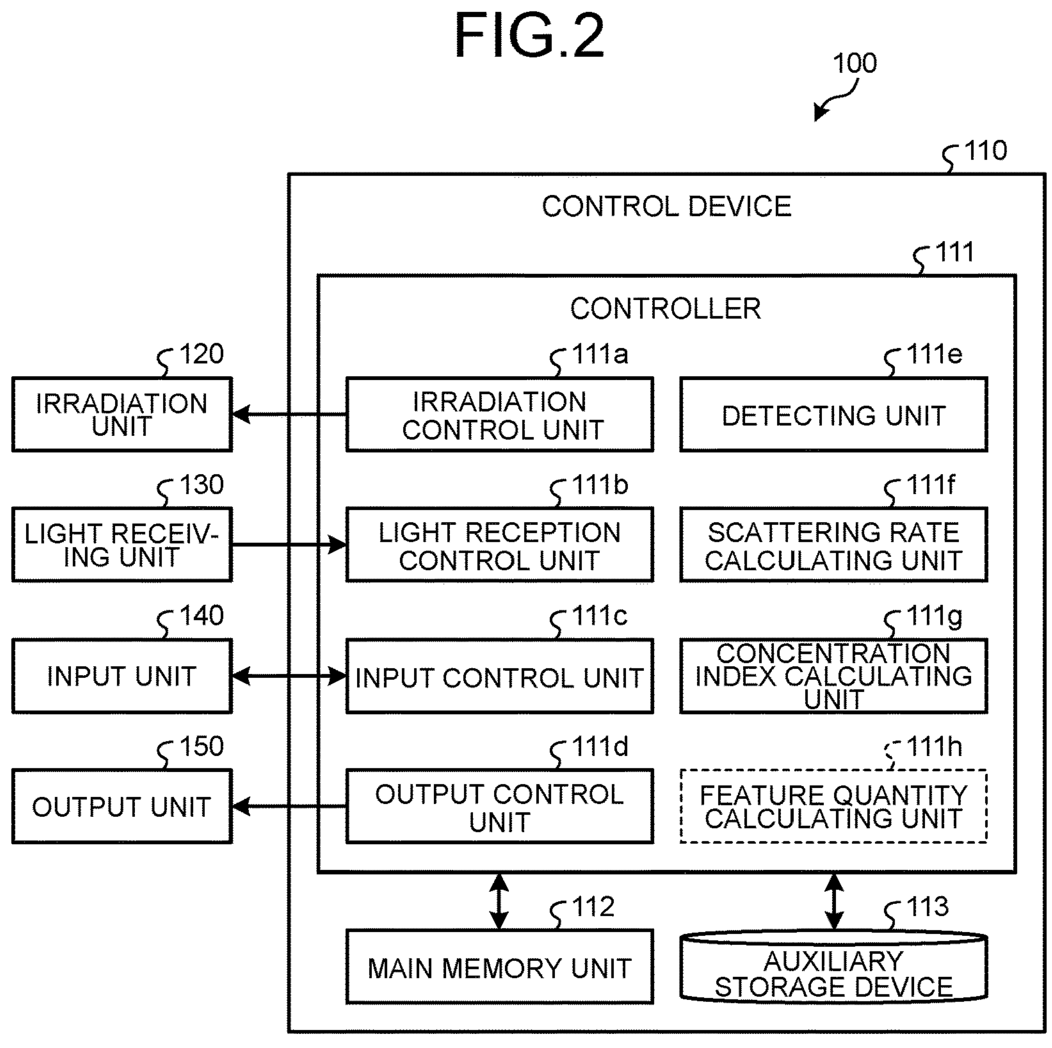
FIG. 2 is a block diagram of a control device of the biological information measurement device according to the first embodiment.

FIG. 2 is a block diagram of the biological information measurement device 100. As illustrated in FIG. 2, apart from including the control device 110, the irradiation unit 120, and the light receiving unit 130; the biological information measurement device 100 also includes an input unit 140 and an output unit 150. The input unit 140 and the output unit 150 build a user interface for the user or the operator. For example, the input unit 140 is an input device such as a keyboard, a touch-sensitive panel, a mouse, switches, or operation buttons. The output unit 150 is an output device such as a display, a printer, a lamp, or a speaker that performs output in the form of images, printed material, or sounds.

The control device 110 includes a controller 111, a main memory unit 112, and an auxiliary storage device 113.

The controller 111 is, for example, a processor (circuit) such as a central processing unit (CPU). The main memory unit 112 is, for example, a random access memory (RAM) or a read only memory (ROM). The auxiliary storage device 113 is a nonvolatile storage device such as a solid state drive (SSD) or a hard disk drive (HDD).

The controller 111 reads programs stored in the main memory unit 112 or the auxiliary storage device 113 and executes them so as to function as an irradiation control unit 111*a*, a light reception control unit 111*b*, an input control unit 111*c*, an output control unit 111*d*, a detecting unit 111*e*, a scattering rate calculating unit 111*f*, and a concentration index calculating unit 111*g*. The programs are installable files or executable files that may be recorded in a computer-readable recording medium. The recording medium may also be referred to as a program product. Meanwhile, the programs, the values used in the arithmetic processing performed in the processor, or information such as maps and tables may be stored in advance in the main memory unit 112 or the auxiliary storage device 113, or may be stored in a computer connected to a communication network and downloaded and stored in the auxiliary storage device 113 via the communication network. The auxiliary storage device 113 is used to store the data written by the processor. Meanwhile, the arithmetic processing performed by the controller 111 may at least partially be implemented using hardware. In that case, the controller 111 may include, for example, an FPGA (Field Programmable Gate Array) or an ASIC (Application Specific Integrated Circuit).

The irradiation control unit 111*a* controls the irradiation unit 120 so as to ensure the output of a predetermined testing light.

The light reception control unit 111*b* controls the light receiving unit 130 so as to ensure the reception of the testing light.

The input control unit 111*c* receives input signals from the input unit 140. Moreover, the input control unit 111*c* may control the input unit 140 so as to enable predetermined input operations.

The output control unit 111*d* controls the output unit 150 so as to ensure a predetermined output.

The inventors did a thorough study and found out that, accompanying an increase in the glucose concentration in the blood, there is an increase in the scattering rate of light in the blood. When light is irradiated onto the blood, due to different refractive indexes of the blood plasma and the blood cells, the light gets scattered at the surface of the blood cells, that is, at the minute asperity of the interfaces representing the boundaries between the blood cells and the blood plasma. Hence, when light is irradiated onto the blood cells, greater the area of the interfaces, the greater is the scattering of the light. The inventors focused on that phenomenon and did a thorough study to find the following: (1) in the abutting portion of two blood cells, since there is no refractive index difference, there is almost no scattering of light; (2) when the glucose concentration is low, the blood cells in the blood remain abutted against each other, so that the interface remains small in area and the scattering of light is less; and (3) as the glucose concentration in the blood increases, the blood cells in the blood move away from each other thereby resulting in an increase in the area of the interface, and accordingly the scattering of light increases. The separation of the blood cells accompanying an increase in the glucose concentration is inferred to be caused by the negative charging of the blood cells.

Using such a phenomenon found out by the inventors, in order to calculate the glucose concentration in the blood 210 based on the scattering of light occurring in the blood 210, the controller 111 according to a first embodiment includes the detecting unit 111*e*, the scattering rate calculating unit 111*f*, and the concentration index calculating unit 111*g*.

The detecting unit 111*e* calculates the received-light intensity as the total value of the luminance values of the pixels of the light receiving element of the light receiving unit 130.

The scattering rate calculating unit 111*f* calculates the scattering rate as, for example, the ratio of the scattering intensity with respect to the irradiating intensity. The irradiating intensity may be considered as the sum of the transmission intensity or the reflection intensity, the absorption intensity, and the scattering intensity. Since the received-light intensity is the intensity of the transmitted light or the reflected light, the scattering intensity may be calculated by subtracting the received-light intensity and the absorption intensity from the irradiating intensity. Herein, the absorption intensity represents the intensity of the testing light that is absorbed in the biological object 200, and may be estimated according to a method explained later. The absorption intensity may be obtained in advance and stored in, for example, the auxiliary storage device 113 as a numerical value or a function in a program or as the data referred to by a program.

The concentration index calculating unit 111*g* calculates a concentration index, which corresponds to the scattering rate calculated at the scattering rate calculating unit 111*f*, based on the pre-obtained correlation between the scattering rate and the concentration index. Herein, the concentration index represents a value serving as the index of the glucose concentration, and either may be the glucose concentration itself or may be a relative value that increases in proportion to an increase in the glucose concentration. The concentration index may be set as an individual value for each person or may be set as a common value for a plurality of persons. Moreover, during the follow-up, as long as the concentration index gives a rough indication of the increase and decrease in the glucose concentration, it serves the purpose.

Figure 3:
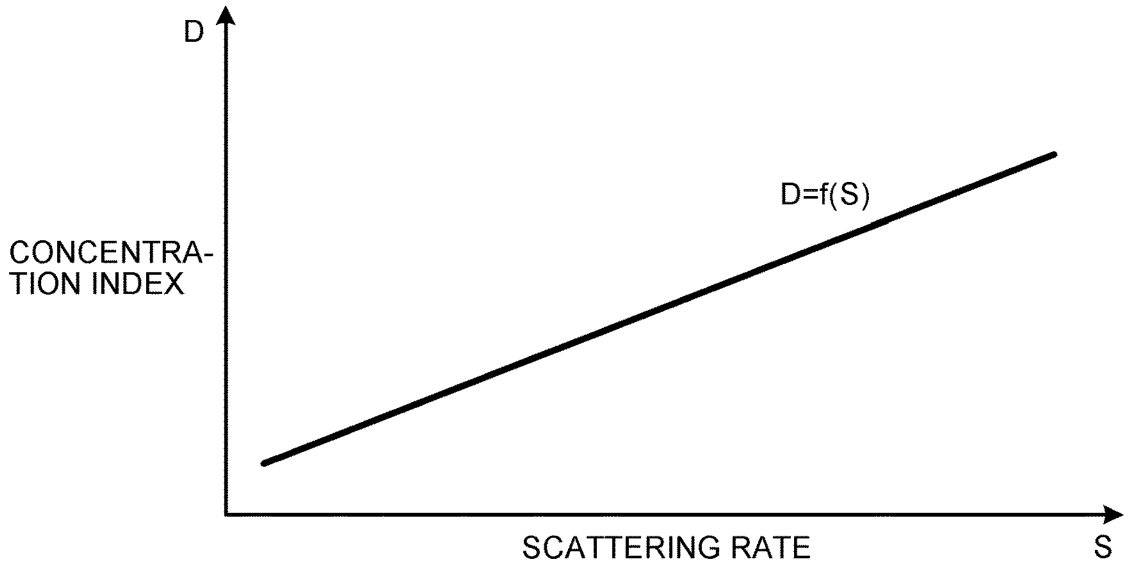
FIG. 3 is a diagram illustrating an exemplary correlation between the scattering rate of light and a concentration index of the target substance in a test material as obtained in the biological information measurement device according to the first embodiment.

FIG. 3 is a diagram illustrating an exemplary correlation between a scattering rate S and a concentration index D. As explained above, as a result of the research done by the inventors, it became clear that the glucose concentration increases in proportion to an increase in the scattering rate S of the testing light. From the test results obtained regarding a plurality of samples, it became clear that the concentration index D corresponding to the glucose concentration may be expressed as an approximation function f(S) of the testing light. Meanwhile, in FIG. 3, the approximation function f(S) is illustrated to be a linear function. However, that is not the only possible case. The correlation explained above is obtained in advance and is stored as a function, or a map, or a table in, for example, the auxiliary storage device 113.

Figures 4, 5:
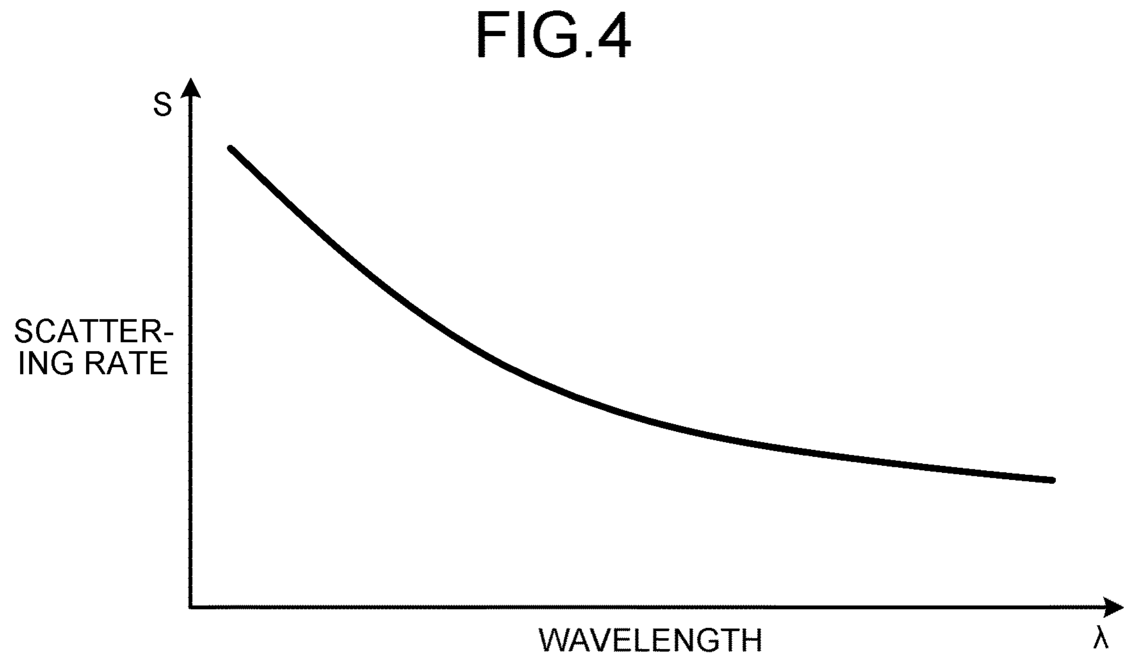
FIG. 4 is a graph illustrating an example of the wavelength characteristics of the scattering rate of light of a test material as obtained in the biological information measurement device according to the first embodiment depending on the wavelength of light.
FIG. 5 is a flowchart for explaining an exemplary sequence of operations performed in the biological information measurement device according to the first embodiment.

In order to perform the measurement based on the new knowledge mentioned above, it is desirable that the testing light output from the irradiation unit 120 is of a wavelength that has a low rate of absorption in the biological object 200, the blood 210, the blood plasma, the blood cells, and the glucose. FIG. 4 is a graph illustrating an example of the wavelength characteristics of the scattering rate with respect to an object or a substance. Regarding the wavelength characteristics of the scattering of light due to the minute asperity at the interfaces between the blood cells and the blood plasma, at a wavelength λ in the wavelength range selected as the testing light as illustrated in FIG. 4, it is believed that the wavelength characteristics do not exhibit any peak. As the wavelength λ of the testing light, for example, a wavelength equal to or greater than 950 [nm] and equal to or smaller than 1100 [nm] is used.

Moreover, in order to ensure that the testing light does not get optically coupled with the blood cells, it is desirable that the wavelength λ of the testing light is equal to or greater than 1/20-th of the depth (diameter) of the blood cells. The diameter of the blood cells is around 10 [μm].

Moreover, in order to perform the measurement, it is desirable that the irradiation unit 120 includes, as the light source device, a surface-emitting element having the in-plane variability of the luminance to be equal to or smaller than 10 [%].

Furthermore, it is desirable that the light receiving unit 130 receives images of such a resolution that the images of the blood cells have distinguishable diameters.

FIG. 5 is a flowchart for explaining an exemplary sequence of operations performed in the biological information measurement device 100. As illustrated in FIG. 5, firstly, the controller 111 functions as the irradiation control unit 111*a* and the light reception control unit 111*b*, and controls the irradiation unit 120 to irradiate the testing light toward the biological object 200 and controls the light receiving unit 130 to receive the testing light coming from the biological object 200 (S1).

Then, the controller 111 functions as the detecting unit 111*e* and calculates the received-light intensity in the light receiving unit 130. The received-light intensity is, for example, the total value of the luminance values of the pixels of the light receiving element of the light receiving unit 130 (S2).

Subsequently, the controller 111 calculates the scattering rate according to the received-light intensity calculated by the detecting unit 111*e* at S2 (S3).

Then, based on the correlation between the scattering rate and the concentration index as illustrated in FIG. 3, the controller 111 calculates the concentration index corresponding to the scattering rate calculated by the scattering rate calculating unit 111*f* at S3 (S4).

Subsequently, the controller 111 functions as the output control unit 111*d* that controls the output unit 150 to output the concentration index (S5). At S5, either the value of the concentration index obtained during the concerned testing may be output, or a graph may be output that indicates the temporal change in the concentration indexes including the concentration indexes calculated during the past testing. In the case of performing such operations, every time the scattering rate is calculated at S3, it may be stored in the auxiliary storage device 113 in a corresponding manner to the ID of the subject being tested and the measurement date and time; and the output control unit 111*d* may refer to the stored information and generate output information to be output from the output unit 150.

Figure 6:
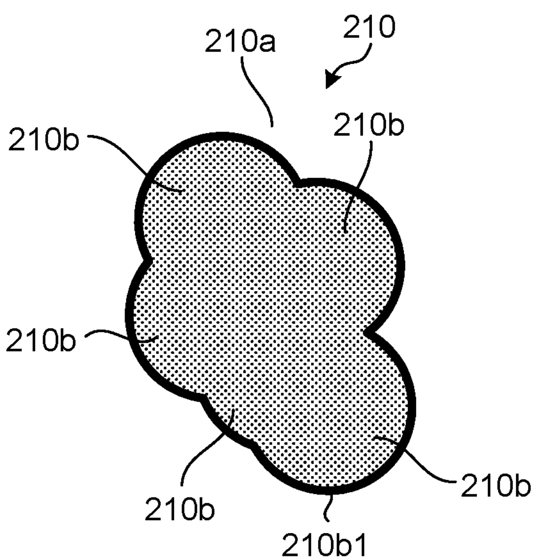
FIG. 6 is an illustrative schematic diagram indicating the state in which particles are closely attached to each other in a two-dimensional image.
Figure 7:
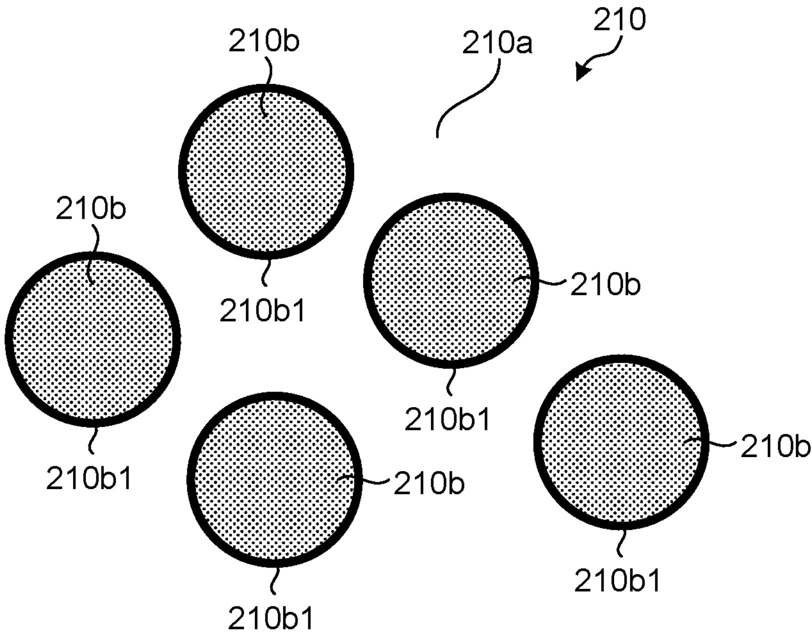
FIG. 7 is an illustrative schematic diagram indicating the state in which particles are separated from each other in a two-dimensional image.

The inventors found out that the absorption intensity of the light in the blood 210 may be estimated based on the analysis of a two-dimensional image of the blood that includes the blood plasma. FIGS. 6 and 7 are schematic diagrams of two-dimensional images of the blood that includes the blood plasma. In FIG. 6 is illustrated an image indicating the state in which the blood cells are closely attached to each other, and in FIG. 7 is illustrated an image indicating the state in which the blood cells are separated from each other. Meanwhile, in FIGS. 6 and 7, although only five blood cells are illustrated, an actual image has a large number of blood cells captured therein.

Apart from the measurement performed by the biological information measurement device 100; for example, image analysis is performed with respect to a microscopic image of the blood 210 that is taken as a sample on a prepared slide. In the image analysis, as a feature quantity of the images of blood cells 210*b*, that is, as the boundary length of the interface between the blood cells and the blood plasma; for example, the total value of the lengths of boundaries 210*b*1 between the blood cells 210*b* and blood plasma 210*a* is obtained in the region onto which the light is irradiated. In that case, for example, a plurality of blood cells 210*b* that is closely attached to each other is grouped as a singular mass in the region corresponding to the blood cells, and the length of the boundary 210*b*1 (edge) obtained as a result of edge detection of each such group is calculated. Thus, if FIG. 6 is compared with FIG. 7, it becomes clear that, in the case in which a plurality of blood cells 210*b* is separated from each other as illustrated in FIG. 7, the total value of the lengths of the boundaries 210*b*1 is greater as compared to the case in which a plurality of blood cells 210*b* is closely attached to each other as illustrated in FIG. 6. Thus, the total value is, for example, the total value of the lengths of a plurality of boundaries 210*b*1 obtained as a result of performing image analysis within a predetermined range of a two-dimensional image. As explained above, when a plurality of blood cells 210*b* is closely attached to each other, the area of the interface between the blood cells 210*b* and the blood plasma 210*a* becomes smaller. When the blood cells are separated from each other, the area of the interface between the blood cells and the blood plasma is equal to $\pi \cdot n \cdot d^2$ (where n represents the number of blood cells and d represents the diameter of the blood cells). On the other hand, when the blood cells are attached to each other, the area of the interface is obtained by subtracting the area of the portions of contact between the blood cells from the area of the interface ($\pi \cdot n \cdot d^2$) in the case in which the blood cells are separated from each other. Approximatively, the diameter d is obtained for the mass in which the blood cells are attached to each other; the interface area of that singular mass is calculated as $\pi \cdot d^2$; and that interface area may be treated as the integrated value equivalent to the number of blood cells in the light irradiation region. In the image analysis, the actual area of the interface between the blood cells 210*b* and the blood plasma 210*a* increases in proportion to an increase in the total value of the lengths of the boundaries 210*b*1; and the actual area of the interface decreases in proportion to a decrease in the total value of the lengths of the boundaries 210*b*1. That is, the total value of the lengths of the boundaries 210*b*1 may serve as a parameter (feature quantity) corresponding to the area of the interface between the blood cells 210*b* and the blood plasma 210*a*, as well as may serve as a parameter corresponding to the scattering rate of light.

Figure 8:
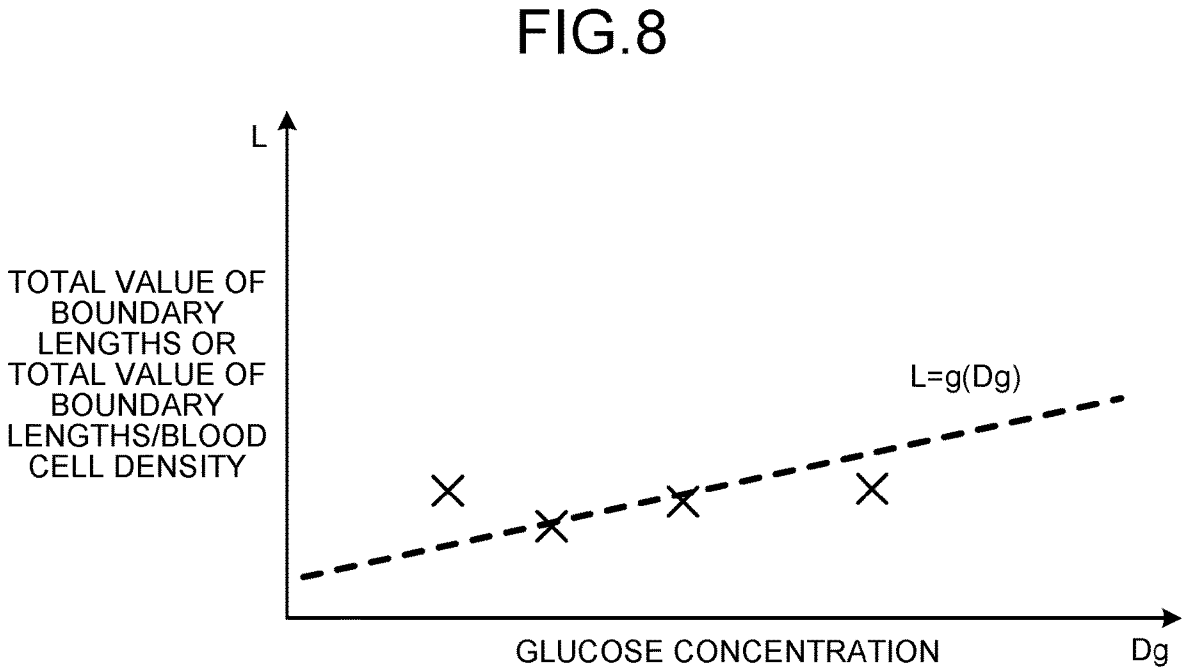
FIG. 8 is a diagram illustrating an exemplary correlation between glucose concentration in a test material and the total value of boundary lengths in a two-dimensional image as obtained in the biological information measurement device according to the first embodiment.

In practice, it was found out that, regarding a glucose concentration Dg and a total value L of the lengths of all boundaries 210*b*1 within the measurement range being irradiated with light, the correlation is as illustrated in FIG. 8. Herein, FIG. 8 is a graph indicating the changes in the total value L of the lengths of the boundaries 210*b*1, which is obtained as a result of performing image analysis, in the case in which the glucose concentration in the blood undergoes changes. By referring to FIG. 8, it may be understood that the blood cells 210*b* move away from each in proportion to an increase in the glucose concentration, and accordingly there is an increase in the total value of the lengths of the boundaries 210*b*1 as obtained by performing image analysis. The boundary length L may be expressed as an approximation function g(Dg) of the glucose concentration Dg. Meanwhile, in FIG. 8, the approximation function g(Dg) is illustrated to be a linear function. However, that is not the only possible case.

Figure 9:
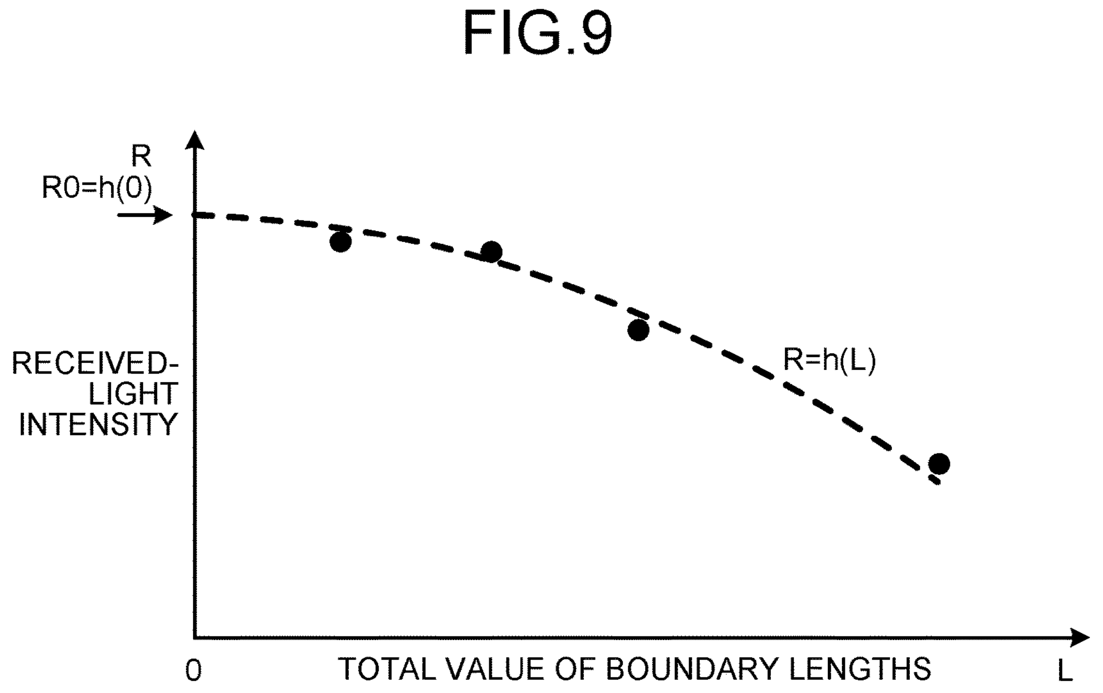
FIG. 9 is a graph that, in the case in which image analysis is performed regarding a plurality of samples for which the received-light intensity is detected in the biological information measurement device according to the first embodiment, indicates an exemplary correlation between the total value of boundary lengths and the received-light intensity which is detected by a detecting unit.

FIG. 9 is a graph that, in the case in which the above-mentioned image analysis is performed regarding a plurality of samples for which the received-light intensity is detected in the biological information measurement device 100, indicates the correlation between the total value L of the lengths of all boundaries 210*b*1 within the measurement range and the received-light intensity which is detected by the detecting unit 111*e*. At that time, the total value L may be a value standardized using the number of blood cells, or the area of the blood cells, or the density of the blood cells. By referring to FIG. 9, it may be understood that a received-light intensity R decreases in inverse proportion to an increase in the total value L of the lengths of the boundaries 210*b*1; and that the received-light intensity R increases in inverse proportion to a decrease in the total value L of the lengths of the boundaries 210*b*1. The received-light intensity R may be expressed as an approximation function h(L) of the total value L of the lengths of the boundaries 210*b*1. The plurality of samples illustrated in FIG. 9 have different total values L of the lengths of the boundaries 210*b*1, that is, have different areas of the interface between the blood cells 210*b* and the blood plasma 210*a*. The approximation function h(L) is obtained as a result of performing regression analysis of a plurality of samples.

The inventors found out that, when the glucose concentration in the blood 210 is low, the total value L of the lengths of the boundaries 210*b*1 becomes equal to zero, that is, the boundaries 210*b*1 are not detected during image analysis. In that case, in the actual blood 210 too, it may be estimated that the blood cells 210*b* are closely attached to each other, the area of the interface is minimum, and there is either substantially no scattering or extremely less scattering of the testing light.

That is, the received-light intensity R in the case in which the total value L of the lengths of the boundaries 210*b*1 is equal to zero, that is, a received-light intensity R0=h(0) (hereinafter, the received-light intensity R0 is treated as the base received-light intensity) corresponds to the case in which the scattering light is the lowest (≈0). The base received-light intensity R0 may be said to be a value calculated by extrapolating the values of a plurality of samples.

The difference obtained by subtracting the base received-light intensity R0 from the irradiation intensity in the case of having the lowest scattering light (≈0) is equivalent to the intensity difference based on pure absorption obtained after the elimination of the effects of the scattering of light attributed to the biological object 200, the blood 210, the blood plasma, the blood cells, glucose, and other substances such as hemoglobin. That is, the abovementioned difference is equivalent to an absorption intensity A. In this way, the absorption intensity A may be estimated. Meanwhile, if the approximation is performed as a quadratic function such as a function $h(L)=a\times L^2\times b\times L+c$, coefficients a and b represent the structural fluctuation at the interface between the blood cells and the blood plasma causing the scattering of light, that is, represent light scattering coefficients. The light scattering coefficients a and b too sometimes undergo changes due to the action with the target substance such as glucose, and may be used as concentration indexes.

Thus, the scattering rate calculating unit 111*f* may subtract the received-light intensity R, which is obtained by the detecting unit 111*e* at each measurement timing, and the absorption intensity A (a constant value) from the irradiation intensity, and calculate the scattering intensity at each measurement timing; and may calculate the scattering rate as the ratio of the scattering intensity with respect to the irradiation intensity. As a result of performing such arithmetic processing, the absorption attributed to the biological object 200, the blood 210, the blood plasma, the blood cells, glucose, and other substances may be taken into account, thereby enabling more accurate calculation of the scattering rate and in turn the concentration indexes.

Meanwhile, the base received-light intensity and the absorption intensity A, which are used in calculating the scattering rate by taking into account the absorption, may be the values obtained by performing on an individual basis. However, the premise for obtaining the values is collecting blood in an invasive manner. Alternatively, values obtained by performing testing on some other person, or average values, or general values, or analytical values may be used in substitution.

Meanwhile, by referring to the graph illustrated in FIG. 8, it may be understood that, based on the correlation between a feature quantity of an image of the blood cells 210*b*, which is obtained by performing image analysis, and the glucose concentration (the concentration index), the glucose concentration may be calculated from the feature quantity of the image. In order to calculate the glucose concentration based on the correlation illustrated in FIG. 8, the biological information measurement device 100 includes, as the light receiving unit 130, an optical system for image analysis, such as an electronic microscope, and a light receiving element; apart from including an optical system for scattering detection and a light receiving element. Moreover, the controller 111 may include a feature quantity calculating unit 111*h* (see FIG. 2) that calculates the feature quantity of an image of the blood cells 210*b* by performing image analysis. In that case, the controller 111 reads programs stored in the main memory unit 112 or the auxiliary storage device 113 and executes them so as to function as the feature quantity calculating unit 111*h* and the concentration index calculating unit 111*g*. The concentration index calculating unit 111*g* uses the approximation function g indicating the correlation illustrated in FIG. 8 or uses a map or a table, and calculates the glucose concentration Dg as the concentration index corresponding to the feature quantity calculated by the feature quantity calculating unit 111*h*. Herein, the function, or the map, or the table is stored in, for example, the auxiliary storage device 13. However, regarding such calculation of the concentration index that corresponds to the feature quantity and that is based on image analysis, the premise is collecting blood in an invasive manner. Hence, it is desirable to perform the calculation in combination with the noninvasive testing based on the scattering intensity as explained earlier.

Meanwhile, the feature quantity of an image of the blood cells 210*b* as used during image analysis is not limited to the total value of the lengths of the boundaries 210*b*1. Alternatively, some other parameter may also be used, such as the number of blood cells 210*b* captured in a two-dimensional image, or the total value of the areas of the images of the blood cells 210*b* in a two-dimensional image, or the density (for example, the area density) of the images of the blood cells 210*b* in a two-dimensional image. The correlation of each feature quantity of the images of the blood cells 210*b* with the concentration index corresponds to the fact that the density of the blood cells 210*b* in the blood plasma 210*a* goes on decreasing in inverse proportion to an increase in the glucose concentration. For example, higher the concentration of glucose, the greater is the decrease in the number of blood cells 210*b* in the two-dimensional image, the greater is the decrease in the total value of the areas of the blood cells 210*b* in the two-dimensional image, and the greater is the decrease in the density of the images of the blood cells 210*b* in the two-dimensional image.

Figure 10:
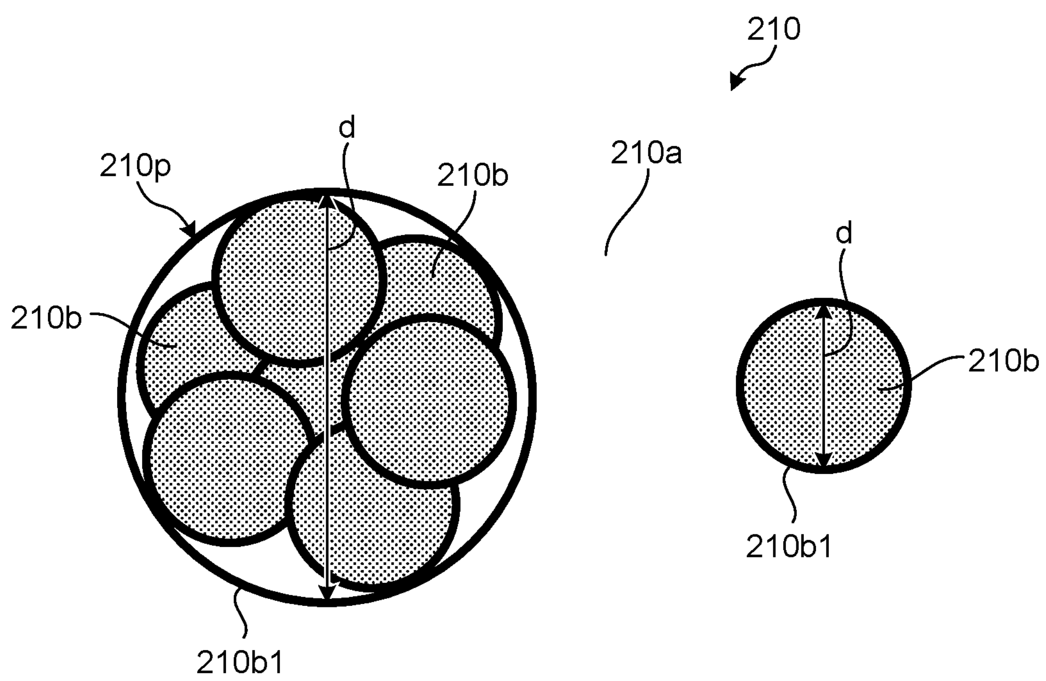
FIG. 10 is an explanatory diagram for explaining an exemplary method for obtaining the diameter of the particles according to the laser diffraction/scattering method.

As a method for obtaining information about the interface area or the boundary length of the interface of the particles in biological objects such as blood cells, it is possible to implement a laser diffraction/scattering method. In that method, different intensity patterns are observed according to the angles of the scattering light, and particle size distribution is obtained using the Mie scattering theory. This method is a widely-used technology in the measurement field. FIG. 10 is an explanatory diagram for explaining an exemplary method for obtaining the diameter d of the blood cells 210*b* according to the laser diffraction/scattering method. As illustrated in FIG. 10, for example, when the blood cells 210*b* are closely attached to each other thereby forming a mass, that mass may approximated to a particle 210*p* and the diameter d may be calculated, and the interface area or the length of the boundary 210*b*1 of the interface may be calculated from the diameter d. Meanwhile, when there is only one blood cell 210*b*, the interface area or the length of the boundary 210*b*1 of the interface may be calculated from the diameter d of that blood cell 210*b*.

Figure 11:
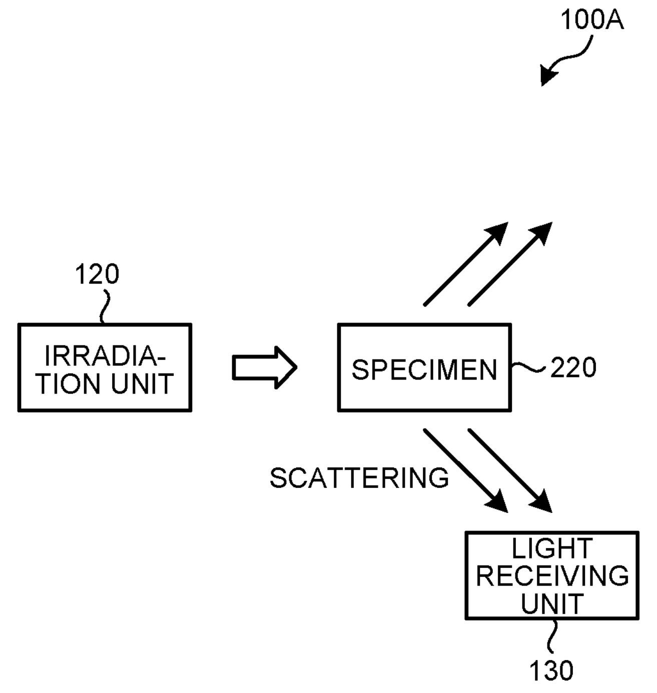
FIG. 11 is an illustrative overall configuration diagram of a biological information measurement device according to a second embodiment.

FIG. 11 is an overall configuration diagram of a biological information measurement device 100A according to a second embodiment. As illustrated in FIG. 11, in the second embodiment, the light receiving unit 130 receives, as the testing light irradiated from the irradiation unit 120 and passing via a specimen 220, the scattering light coming from the specimen 220. In that case, the ratio of the scattering light receivable by the light receiving unit 130 with respect to the scattering light going out in all directions from the specimen 220 is obtained in advance, so that the scattering rate calculating unit 111*f* (see FIG. 2) becomes able to easily calculate the scattering rate of light according to the received-light intensity of the testing light received in the light receiving unit 130. The subsequent operations are identical to the operations according to the first embodiment explained above.

As explained above, according to the second embodiment, the glucose concentration in the blood 210 may be calculated based on the scattering rate of the testing light. With such a configuration, if the scattering rate of the testing light is used, the glucose concentration may be measured with a higher degree of accuracy.

For example, a substance other than the blood may also be used as the test material.

According to the present disclosure, it becomes possible to provide a biological information measurement device, a biological information measurement method, and a program in a new and improved form, so that the concentration of the target substance may be measured even using laser light having the wavelength not absorbable by the target substance.

The present disclosure may be implemented in a biological information measurement device, a biological device measurement method, and a program.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A biological information measurement device comprising:

a scattering rate calculating unit configured to calculate a scattering rate of light at an interface between a medium present in a biological object or in a specimen and a particle included in the medium based on received-light intensity of light irradiated onto the biological object or onto the specimen and received via the biological object or via the specimen; and a concentration index calculating unit configured to calculate, based on a correlation between the scattering rate of the light at the interface and a concentration index corresponding to concentration of a target substance that is different from the particle included in the medium, the concentration index corresponding to the scattering rate of the light calculated by the scattering rate calculating unit, wherein the scattering rate calculating unit is configured to calculate the scattering rate of light based on base received-light intensity R0 that represents received-light intensity of light when scattering in the medium is minimum or substantially equal to zero.

2. The biological information measurement device according to claim 1, wherein the light irradiated onto the biological object or the specimen is light of a wavelength that does not exhibit peak of the absorption rate in wavelength characteristics of absorption rates of light in the medium, the particle and the target substance.

3. The biological information measurement device according to claim 1, wherein the target substance is glucose, and the concentration index calculating unit configured to calculate the concentration index based on the correlation between the scattering rate of the light calculated by the scattering rate calculating unit and a concentration index corresponding to concentration of glucose.

4. The biological information measurement device according to claim 1, wherein the medium is blood plasma, and the base received-light intensity is calculated by extrapolating correlation of received-light intensity of light with an area of interface or a boundary length of interface in a plurality of samples having different areas of interface between the particle included in the medium and the medium.

5. The biological information measurement device according to claim 1, wherein the particle is a blood cell.

6. The biological information measurement device according to claim 1, wherein the scattering rate calculating unit is configured to calculate the scattering rate of light at the interface between the medium present in the biological object or in the specimen and the particle included in the medium based on received-light intensity of light passed through the biological object or the specimen or based on received-light intensity of light reflected from the biological object or the specimen, and the received-light intensity is calculated as a total value of luminance values of pixels of a light receiving element of a light receiving unit.

7. The biological information measurement device according to claim 1, wherein the scattering rate calculating unit is configured to calculate the scattering rate of light based on the base received-light intensity R0 that represents received-light intensity of light when scattering in the medium is minimum or substantially equal to zero, the base received-light intensity R0 is received-light intensity R in the case in which a total value L of lengths of boundaries of the interfaces is equal to zero, a difference obtained by subtracting the base received-light intensity R0 from an irradiation intensity in the case of having lowest scattering light is equivalent to an absorption intensity A, and the scattering rate calculating unit calculates the scattering intensity by subtracting the received-light intensity R and the absorption intensity A from the irradiation intensity, and calculates the scattering rate as a ratio of the scattering intensity with respect to the irradiation intensity.

8. The biological information measurement device according to claim 7, wherein the base received-light intensity is calculated by extrapolating correlation of received-light intensity of light with an area of interface or a boundary length of interface in a plurality of samples having different areas of interface between the particle included in the medium and the medium.

9. The biological information measurement device according to claim 8, wherein, as the plurality of samples having different areas of interface, a plurality of samples are used each of which has a different feature quantity regarding the area of interface or the boundary length of interface in a particle image obtained as a result of performing image processing on a two-dimensional image of the medium including the particle and the target substance.

10. The biological information measurement device according to claim 9, wherein feature quantity regarding the area of interface or the boundary length of interface in the particle image is a total value of edge lengths of the particle images, number of the particle images, a total value of areas of the particle images, or density of the particle images in the two-dimensional image.

11. The biological information measurement device according to claim 8, wherein the feature quantity regarding the area of interface or the boundary length of interface is calculated based on a diameter of the particle measured using laser diffraction/scattering method.

12. The biological information measurement device according to claim 1, wherein the scattering rate calculating unit is configured to calculate the scattering rate of the light at the interface between the medium present in the biological object or in the specimen and the particle included in the medium based on the received-light intensity of light scattered from the biological object or the specimen.

13. The biological information measurement device according to claim 1, further comprising:

an irradiation unit configured to irradiate a biological object or a specimen with light;

a light receiving unit configured to receive the light irradiated onto the biological object or onto the specimen from the irradiation unit and passed via the biological object or via the specimen; and a detecting unit configured to detect received-light intensity of the light received by the light receiving unit.

14. The biological information measurement device according to claim 13, wherein the irradiation unit includes a surface-emitting element having in-plane variability of luminance to be equal to or smaller than 10%.

15. The biological information measurement device according to claim 13, wherein the irradiation unit includes a light source configured to output light having a wavelength equal to or greater than 1/20-th of a depth of the particle.

16. The biological information measurement device according to claim 13, wherein the light receiving unit is configured to receive an image having resolution in which a diameter of an image of the particle is distinguishable.

17. The biological information measurement device according to claim 13, further comprising a field lens configured to allow passage of light received by the light receiving unit.

18. A biological information measurement method executed by a computer, the method comprising:

calculating a scattering rate of light at an interface between a medium present in a biological object or in a specimen and a particle included in the medium based on received-light intensity of light irradiated onto the biological object or onto the specimen and received via the biological object or via the specimen; and calculating the concentration index as biological information calculating performing correction in form of subtracting the calculated scattering rate of light based on a correlation stored in a memory and established between the scattering rate of light at the interface and a concentration index corresponding to concentration of a target substance that is different from the particle included in the medium, wherein in the calculating the scattering rate of light, calculating the scattering rate of light based on base received-light intensity R0 that represents received-light intensity of light when scattering in the medium is minimum or substantially equal to zero, is used.

19. A non-transitory computer-readable recording medium on which an executable program causing a processor of a computer to execute:

calculating a scattering rate of light at an interface between a medium present in a biological object or in a specimen and a particle included in the medium based on received-light intensity of light irradiated onto the biological object or onto the specimen and received via the biological object or via the specimen; and calculating, based on a correlation between the scattering rate of the light at the interface and a concentration index corresponding to concentration of a target substance that is different from the particle included in the medium, the concentration index corresponding to the calculated scattering rate of the light, wherein in the calculating the scattering rate of light, calculating the scattering rate of light based on base received-light intensity R0 that represents received-light intensity of light when scattering in the medium is minimum or substantially equal to zero, is used.

* * * * *